United States Patent
Haber et al.

(10) Patent No.: US 9,821,061 B2
(45) Date of Patent: Nov. 21, 2017

(54) ENHANCED PLASMONIC NANOPARTICLES FOR CANCER THERAPY AND DIAGNOSTICS

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: Louis Hamilton Haber, Baton Rouge, LA (US); Tony Eugene Karam, Baton Rouge, LA (US); Holden Tyler Smith, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 15/060,180

(22) Filed: Mar. 3, 2016

(65) Prior Publication Data

US 2016/0256548 A1   Sep. 8, 2016

Related U.S. Application Data

(60) Provisional application No. 62/127,325, filed on Mar. 3, 2015.

(51) Int. Cl.
| | |
|---|---|
| *B82Y 5/00* | (2011.01) |
| *A61K 41/00* | (2006.01) |
| *B82Y 15/00* | (2011.01) |
| *B82Y 30/00* | (2011.01) |
| *A61K 47/48* | (2006.01) |

(52) U.S. Cl.
CPC .... *A61K 41/0052* (2013.01); *A61K 47/48861* (2013.01); *B82Y 5/00* (2013.01); *B82Y 15/00* (2013.01); *B82Y 30/00* (2013.01)

(58) Field of Classification Search
CPC ............ B82Y 5/00; B82Y 15/00; B82Y 30/00
See application file for complete search history.

(56) References Cited

U.S. PATENT DOCUMENTS

| | | |
|---|---|---|
| 8,343,627 B2 | 1/2013 | Zhong et al. |
| 8,605,280 B2 | 12/2013 | Heck et al. |

(Continued)

FOREIGN PATENT DOCUMENTS

| | | |
|---|---|---|
| CN | 105194693 A | 12/2015 |
| WO | WO 03008539 A2 | 1/2003 |

OTHER PUBLICATIONS

PCT International Search Report, International Application PCT/US2016/020704, dated Jun. 22, 2016, 4 pages.

(Continued)

*Primary Examiner* — Carlos Azpuru
(74) *Attorney, Agent, or Firm* — Tucker Ellis LLP; Michael Craig

(57) ABSTRACT

One or more techniques and/or products are disclosed using a process for preparing metallic nanoparticles. Resulting nanoparticles may comprise a gold-silver-gold core-shell-shell nanoparticles. Such nanoparticles can be formed by forming a gold core, providing certain materials to form a silver shell, and providing certain materials to form a gold shell. The metallic nanoparticles may be used in molecular sensing, catalysis, photothermal therapy, and other biologically-relevant technologies.

7 Claims, 10 Drawing Sheets

(56) References Cited

U.S. PATENT DOCUMENTS

| | | |
|---|---|---|
| 2002/0187347 A1 | 12/2002 | Halas et al. |
| 2009/0326614 A1 | 12/2009 | El-Sayed et al. |
| 2013/0261444 A1 | 10/2013 | Green et al. |

OTHER PUBLICATIONS

PCT Written Opinion of the International Searching Authority, International Application PCT/US2016/020704, dated Jun. 2, 2016, 9 pages.

Notification of the Transmittal of the International Search Report and the Written Opinion of the International Searching Authority, or the Declaration, PCT Application PCT/US2016/020704, dated Jun. 22, 2016, 2 pages.

Kiaohua Huang et al., "Cancer Cell Imaging and Photothermal Therapy in the Near-Infrared Region by Using Gold Nanorods," The Journal of American Chemical Society Articles, Jan. 21, 2006, 128, pp. 2115-2120.

Ximei Qian et al., "In vivo tumor targeting and spectroscopic detection with surface-enhanced Raman nanoparticle tags," Nature Biology Articles, Jan. 2008, pp. 83-90, vol. 26, No. 1, Nature Publishing Group.

Geoffrey Von Maltzahn et al., "Computationally Guided Photothermal Tumor Therapy Using Long-Circulating Gold Nanorod Antennas," Cancer Research, May 1, 2009, pp. 3892-3900, vol. 69, No. 9, DOI: 10.1158/0008-5472. CAN-08-4242.

Jennifer L. West et al., "Engineered Nanomaterials for Biophotonics Applications: Improving Sensing, Imaging, and Therapeutics," Annual Review of Biomedical Engineering, 2003, pp. 285-292, vol. 5, DOI: 10.1146/annurev.bioeng.5.011303.120723.

Cheng Xu et al., "Targeting Chemophotothermal Therapy of Hepatoma by Gold Nanorods/Graphene Oxide Core/Shell Nanocomposites," Applied materials & Interfaces, Nov. 25, 2013, pp. 12911-12920, vol. 5, American Chemical Society, DOI: 10.1021/am404714w.

Won II Choi et al., "Tumor Regression in Vivo by Photothermal Therapy Based on Gold-Nanorod-Loaded, Functional Nanocarriers," ACS NANO, 2011, pp. 1995-2003, vol. 5, No. 3, DOI: 10.1021/nn103047r.

Dong-Kwon Lim et al., "Enhanced Photothermal Effect of Plasmonic Nanoparticles Coated with Reduced Graphene Oxide," NANO Letters, Jul. 30, 2013, pp. 4075-4079, vol. 13, American Chemical Society, DOI: 10.1021/nl4014315.

Rizia Bardhan et al., "Theranostic Nanoshells: From Probe Design to Imaging and Treatment of Cancer," Accounts of Chemical Research, May 25, 2011, pp. 936-946, vol. 44, No. 1, American Cancer Society, DOI: 10.1021/ar200023x.

Ciceron Ayala-Orozco et al., "Au Nanomatryoshkas as Efficient Near-Infrared Photothermal Transducers for Cancer Treatment: Benchmarking against Nanoshells," ACS NANO, Jun. 3, 2014, pp. 6372-6381, vol. 8, No. 6, DOI: 10.1021/nn501871d.

Megan A. Mackey et al., "The Most Effective Gold Nanorod Size for Plasmonic Photothermal Therapy: Theory and In Vitro Experiments," The Journal of Physical Chemistry, Jan. 16, 2014, pp. 1319-1326, vol. 118, DOI: 10.1021/jp409298f.

Raju R. Kumal et al., "Determination of the Surface Charge Density of Colloidal Gold Nanoparticles Using Second Harmonic Generation," The Journal of Physical Chemistry, Jun. 18, 2015, pp. 16200-16207, vol. 119, DOI: 10.1021/acs/jpcc.5b00568.

Fredrick W. Vance et al., "Enormous Hyper-Rayleigh Scattering from Nanocrystalline Gold Particle Suspensions," The Journal of Physical Chemistry, Nov. 24, 1998, pp. 10091-10093, vol. 102, No. 50, DOI: 10.1021/p984044u.

R. Tuinier, "Approximate solutions to the Poisson-Boltzmann equation in spherical and cylindrical geometry," The Journal of Colloid Interface Science—Science Direct, 2003, pp. 45-49, vol. 258, DOI: 10.1016/S0021-9797(02)00142-X.

Tony E. Karam et al., "Enhanced Photothermal Effects and Excited-State Dynamics of Plasmonic Soze-Controlled Gold-Silver-Gold Core-Shell-Shell Nanoparticles," The Journal of Physical Chemistry, Jul. 17, 2015, pp. 18573-18580, vol. 119, American Chemical Society, DOI: 10.1021/acs.jpcc.5b05110.

S. Freddi et al., "Excited-State Lifetime Assay for Protein Detection on Gold Colloids-Fluorophore Complexes," The Journal of Physical Chemistry, Jan. 26, 2009, pp. 2722-2730, vol. 113, No. 7, American Chemical Society, DOI: 10.1021/jp8095264.

Jibin Song et al., "Self-Assembled Plasmonic Vesicles of SERS-Encoded Amphiphilic Gold Nanoparticles for Cancer Cell Targeting and Traceable Intracellular Drug Delivery," Jul. 25, 2012, pp. 13458-13469, vol. 134, American Chemical Society, DOI: 10.1021/ja305154a.

Ivan H. El-Sayed et al., "Selective laser photo-thermal therapy of epithelial carcinoma using anti-EGFR antibody conjugated gold nanoparticles," Caber Letters—Science Direct, Jul. 29, 2005, pp. 129-135, vol. 239, DOI: 10.1016/i.canlet.2005.07.035.

Temer S. Ahmadi et al., "Picosecond Dynamics of Colloidal Gold Nanoparticles," The Journal of Physical Chemistry, Mar. 14, 1996, pp. 8053-8056, vol. 100, No. 20, American Chemical Society.

Radha Narayannan et al., "Catalysis with Transition Metal Nanoparticles in Colloidal Solution: Nanoparticle Shape Dependence and Stability," The Journal of Physical Chemistry, Jun. 4, 2005, pp. 12663-12676, vol. 109, No. 26, American Chemical Society.

Joseph Callaway, "Model for Lattice Thermal Conductivity at Low Temperatures," Physical Review, Feb. 15, 1959, pp. 1046-1051, vol. 113, No. 4, Pittsburgh, PA.

Steven D. Perrault et al., "Synthesis and Surface Modification of Highly Monodispersed, Spherical Gold Nanoparticles of 50-200 nm," The Journal of American Chemistry Society, 2009, pp. 17042-17043, vol. 131, No. 47, American Cancer Society, DOI: 10.1021/ja907069u.

Marie-Christine Daniel et al., "Gold Nanoparticles: Assembly, Supramolecular Chemistry, Quantum-Sized Properties, and Applications toward Biology, Catalysis, and Nanotechnology," Chemical Reviews, Dec. 20, 2003, pp. 293-346, vol. 104, No. 1, American Chemical Society, DOI: 10.1021/cr030698.

Ivan H. El-Sayed et al., "Surface Plasmon Resonance Scattering and Absorption of anti-EGFR Antibody Conjugated Gold Nanoparticles in Cancer Diagnostics: Applications in Oral Cancer," NANO Letters, 2005, pp. 829-834, vol. 5, No. 5, American Cancer Society, DOI: 10.1021/nl050074e.

S. Link et al., "Femtosecond transient-absorption dynamics of colloidal gold nanorods: Shape independence of the electron-phonon relaxation time," Physical Review B, Mar. 1, 2000, pp. 6086-6090, vol. 61, No. 9, The American Physical Society.

Rizia Bardhan et al., "Fluorescence Enhancement by Au Nanostructures: Nanoshells and Nanorods," ACS NANO, 2009, pp. 744-752, vol. 3, No. 3, American Cancer Society, DOI: 10.1021/ar200023x.

Joseph R. Cole et al., "Photothermal Efficiencies of Nanoshells and Nanorods for Clinical Therapeutic Application," The Journal of Physical Chemistry, Jun. 11, 2009, pp. 12090-12094, vol. 113, No. 28, American Cancer Society, DOI: 10.1021/jp9003592.

Tony E. Karam et al., "Molecular Adsorption and Resonance Coupling at the Colloidal Gold Nanoparticulars Interface," The Journal of Physical Chemistry, Dec. 16, 2013, pp. 642-649, vol. 118, American Cancer Society, DOI: 10.1021/jp410128v.

José H. Hodak al., "Spectroscopy and Dynamics of Nanometer-Sized Noble Metal Particles," The Journal of Physical Chemistry, Aug. 15, 1998, pp. 6958-6967, vol. 102, No. 36, American Cancer Society.

Prashant V. Kamat, "Photophysical, Photochemical and Photocatalytic Aspects of Metal Nanoparticles," The Journal of Physical Chemistry, Jul. 18, 2002, pp. 7729-7744, vol. 106, No. 32, American Cancer Society, DOI: 10.1021/jp0209289.

Prashant V. Kamat, "Meeting the Clean Energy Demand: Nanostructure Architectures for Solar Energy Conversion," The Journal of Physical Chemistry, Feb. 1, 2007, pp. 2834-2860, vol. 111, No. 7, American Cancer Society, DOI: 10.1021/jp066952u.

Manabendra Chandra et al., "Controlled Plasmon Resonance Properties of Hollow Gold Nanosphere Aggregates," The Journal of

(56) References Cited

OTHER PUBLICATIONS

American Chemical Society, Oct. 20, 2020, pp. 15782-15789, vol. 132, No. 44, American Chemical Society, DOI: 10.1021/ja106910x.
A. Knauer et al., "Au/Ag/Au double shell nanoparticles with narrow size distribution obtained by continuous micro segmented flow synthesis," Chemical Engineering Journal, 2011, pp. 1164-1169, vol. 166, Elsevier B.V., DOI: 10.1016/j.cej.2010.12.028.
Marites P. Melancon et al., "In Vitro and in vivo targeting of hollow gold nanshells directed at epidermal growth factor receptor for photothermal ablation therapy," Molecular Cancer Therapeutics, Jun. 2008, pp. 1730-1739, vol. 7, No. 6, American Association for Cancer Research, DOI: 10.1158/1535-7163.MCT.08-0016.
Wolfgang Eck et al., "PEGylated Gold Nanoparticles Conjugated to Monoclonal F19 Antibodies as Targeted Labeling Agents for Human Pancreatic Carcinoma Tissue," ACS NANO, 2008, pp. 2263-2272, vol. 2, No. 11, American Chemical Society, DOI: 10.1021/nn800429d.
Andrew E. Prigodich et al., "Tailoring DNA Structure to Increase Target Hybridization Kinetics on Surfaces," The Journal of American Chemical Society, 2010, pp. 10638-10641, vol. 132, No. 31, American Chemical Society, DOI: 10.1021/ja104859j.
Nikhil R. Jana et al., "Evidence for Seed-Mediated Nucleation in the Chemical Reduction of Gold Salts to Gold Nanoparticles," Chemical Materials, Jun. 22, 2001, pp. 2313-2322, vol. 13, No. 7, American Chemical Society, DOI: 10.1021lcm000662n.
Kenneth R. Brown et al., "Seeding of Colloidal Au Nanoparticle Solutions. 2. Improved Control of Particle Size and Shape," Chemical Materials, Dec. 29, 1999, pp. 306-313, vol. 12, No. 2, American Chemical Society, DOI: 10.1021/cm980065p.
Arunima Coomar et al., "Near-field: A finite-difference time-dependent method for simulation of electrodynamics on small scaled," The Journal of Chemical Physics, 2011, pp. 084121-1-084121-8, vol. 135, DOI: 10.1063/1.3626549.
Dustin J. Maxwell et al., "Self-Assembled Nanoparticle Probes for Recognition and Detection of Biomolecules," The Journal of American Chemistry Society, 2002, pp. 9606-9612, vol. 124, No. 32, American Chemical Society, DOI: 10.1021/ja025814p.
Ralph A. Sperling et al., "Biological applications of golf nanoparticles," Chemical Society Reviews, Jul. 17, 2008, pp. 1896-1908, vol. 37, No. 9, The Royal Society of Chemistry, DOI: 10.1039/b712170a.
Akshaya K. Samal et al., "Size Tunable Au@Ag Core-Shell Nanoparticles: Synthesis and Surface-Enhanced Raman Scattering Properties," 2013, pp. 15076-15082, vol. 29, American Chemical Society, DOI: 10.1021/a403707j.
Amanda J. Haes et al., "A Nanoscale Optical Biosensor: Sensitivity and Selectivity of an Approach Based on the Localized Surface Plasmon Resonance Spectroscopy of Triangular Silver Nanoparticles," The Journal of American Chemical Society, 2002, pp. 10596-10604, vol. 124, No. 35, American Chemical Society, DOI: 10.1021/ja020393x.
Sarah D. Brown et al., "Gold Nanoparticles for the Improved Anticancer Drug Delivery of the Active Component of Oxaliplatin," The Journal of American Chemical Society, 2010, pp. 4678-4684, vol. 132, No. 13, American Chemical Society, DOI: 10.1021/ja908117a.
S.L. Logunov et al., "Electron Dynamics of Passivated Gold Nanocrystals Probed by Subpicosecond Transient Absorption Spectroscopy," The Journal of Physical Chemistry, Apr. 1, 1997, pp. 3713-3719, vol. 101, No. 19, American Chemical Society.
Sara E. Skrabalak et al., "Gold Nanocages for Biomedical Applications," Advanced Materials, 2007, pp. 3177-3184, vol. 19, Wiley InterScience, DOI: 10.1002/adma.200701972.
Kuai Yu et al., "Excitation Wavelength and Fluence Dependent Femtosecond Transient Absorption Studies on Electron Dynamics of Gold Nanorods," The Journal of Physical Chemistry, Jan. 11, 2011, pp. 3820-3826, vol. 115, ACS Publications, DOI: 10.1021/jp108176h.
Adam M. Schwartzberg et al., "Synthesis, Characteristics, and Tunable Optical Properties of Hollow Gold Nanospheres," The Journal of Physical Chemistry, Jun. 29, 2006, pp. 19935-19944, vol. 110, No. 40, American Chemical Society, DOI: 10.1021/jp062136a.

ENHANCED PLASMONIC NANOPARTICLES FOR CANCER THERAPY AND DIAGNOSTICS

This application claims priority to provisional patent application, U.S. Ser. No. 62/127,325, entitled ENHANCED PLASMONIC NANOPARTICLES FOR CANCER THERAPY AND DIAGNOSTICS, filed Mar. 3, 2015, which is incorporated herein by reference.

BACKGROUND

Metallic nanoparticles composed of gold and silver may possess desired chemical, electronic, and optical properties, including an ability for size-controlled synthesis, stabilization, functionalization, and bio-compatibility. Due to these properties, metallic nanoparticles may allow for desired applications in the fields of molecular sensing, catalysis, photothermal therapy, and biologically-relevant technologies, such as bio-imaging and bio-sensing. For example, photothermal therapy may provide a non-invasive approach that can have fewer side effects than conventional treatment, such as chemotherapy and/or radiation therapy. A variety of plasmonic metallic nanoparticles may have potential use in photothermal therapy, including gold nanorods, silver nanorods, gold nanocages, silica-gold core-shell, and gold nanoparticles coated with reduced graphene oxide. Photothermal therapy may utilize plasmonic nanoparticles with near-infrared wavelength absorption in the ranging from about 800 nm to about 1300 nm. Due to the plasmonic enhancement of the metallic portions of the nanoparticle, these nanoparticles can absorb light in the near-infrared wavelengths, corresponding to the optical window in biological tissues. The nanoparticles can convert the absorbed light into heat through a nonradiative process leading to a localized photothermal effect that can be used for photothermal therapy, and/or non-invasive bio-imaging due to their tunable optical properties and their biocompatibility.

Metallic nanoparticles may be difficult to synthesize and keep stable in colloidal suspensions, and some inherent properties of the metals or other materials used in the nanoparticles may present limitations. As an example, spherical gold nanoparticles may possess a very low light absorbance at near-infrared wavelengths, so they may not be preferred for potential biological applications, such as photothermal therapy and diagnostics. In another example, the thickness of the nanoparticle, which can affect its properties and potential applications, may be difficult to control in processing. In yet another example, if a nanoparticle comprises a non-metallic portion, such as gold-coated silica nanoparticles, the resulting particle may have a smaller plasmonic enhancement property than metallic nanoparticles, due to their non-metallic core. Although silica-based plasmonic nanoparticles may have desirable light absorbance at near-infrared wavelengths, their non-fully metallic composition can reduce their conversion of light to heat efficiency, which can make them less effective in killing cancer cells. In another example, both gold-reduced graphene oxide nanoparticles and gold nanorods may absorb at the near-infrared wavelength window. However, synthesis of a uniform reduced graphene oxide shell can be difficult, reproducibility of the gold nanorods may be difficult, and the gold nanorods can be unstable over long period of times.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

In one implementation, one or more techniques and/or products are disclosed for preparing metallic nanoparticles comprising: 1) adding a first citrate compound to a gold solution resulting in a gold core solution comprising at least one gold core; 2) adding ascorbic acid, a silver compound, and a strong base to the gold core solution resulting in a silver shell on at least one gold core; and 3) adding a second citrate compound, hydroquinone, and gold compound to at least one silver shell on at least one gold core resulting in an outer gold shell on the silver shell.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein.

DETAILED DESCRIPTION

Figure 1:
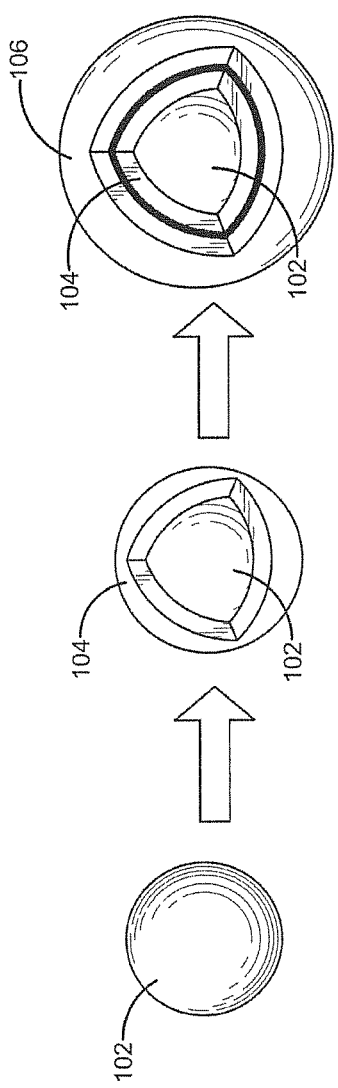
FIG. 1 is a flow diagram illustrating a process for the synthesis of nanoparticles, which is disclosed herein.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter. FIG. 1 provides a process for preparing nanoparticles that may provide the plasmonic enhancement of both gold and silver nanoparticles. Nanoparticles may be particles that range in size from about 1 nm to about 100 nm. Nanoparticles may also be different shapes, including but not limited to, spheres, rods, cubes, and discs. The process illustrated in FIG. 1 is a method of making gold-silver-gold core-shell-shell nanoparticles. The metallic nanoparticles may provide plasmon-enhanced absorption in the near-infrared (NIR) photon energies and may offer opportunities for biologically relevant applications. In one implementation, the metallic nanoparticles prepared by the process illustrated in FIG. 1 may be used for biologically relevant applications including photothermal cancer therapy and biosensing for applications in biolabeling, drug delivery, non-invasive bioimaging, and photothermal therapy.

In certain applications, the nanoparticles may absorb light in the NIR wavelengths and convert it to heat through non-radiative processes, which may lead to a localized photothermal effect. In one implementation, the gold-silver-gold core-shell-shell nanoparticle, as shown in FIG. 1, may allow for improved localized heating effects, which may result from the gold and silver composition, when compared to alternate nanomaterials. In the process illustrated in FIG. 1, the NIR photothermal efficiency may be altered, either increasing or decreasing, in order to provide certain desired biologically relevant applications. In one implementation, the thicknesses of the gold core, silver shell, and gold shell may alter the NIR photothermal efficiency. In another implementation, the ratio of the outer gold shell thickness to the overall particle size may show a linear dependence with the position of the plasmon extinction peak wavelength and may alter the NIR photothermal efficiency. Further, the gold-silver-gold core-shell-shell metallic nanoparticles illustrated may comprise tunable optical properties that have a higher light absorption in the near-infrared wavelength optical window; and the nanoparticles may exhibit plasmonic enhancement and controllable extinction spectra extending from the ultraviolet (UV) to the near-infrared absorption wavelengths. In this example implementation, FIG. 1 illustrates a series of steps in which a gold core 102 is provided. A silver shell 104 is formed around the gold core 102. Additionally, an outer gold shell 106 is formed around the silver shell 104.

In one implementation of FIG. 1, techniques are disclosed for a process of preparing nanoparticles comprising: 1) adding citrate compound to a gold solution resulting in a gold core solution comprising at least one gold core 102; 2) adding ascorbic acid, a silver compound, and a strong base to the gold core solution resulting in a silver shell 104 on at least one gold core 102; and 3) adding a second citrate compound, hydroquinone, and a gold compound to at least one silver shell 104 on at least one gold core 102 resulting in an outer gold shell 106 on the silver shell 104.

In another implementation of the process provided in FIG. 1, twelve nanometer (12 nm) gold nanoparticles may be prepared by reducing $Au^{3+}$ ($HAuCl_{4(aq)}$) to $Au^0$ using sodium citrate in water under boiling conditions to form a gold core 102. Further, a silver shell 104 may be formed around the gold core 102 by reducing $Ag^{2+}$ to $Ag^0$ using L-ascorbic acid under basic aqueous conditions at room temperature. The forming of a silver shell 104 may be iterated at least until an appropriate desired thickness of the silver shell 104 is obtained. Additionally, an outer gold shell 106 may be formed around the silver shell 104 (e.g., or respective silver shells) by reducing $Au^{3+}$ to $Au^0$ using sodium citrate and hydroquinone in water at room temperature. The thickness of the outer gold shell 106 may be controlled by varying the concentrations of $Au^{3+}$ and hydroquinone in solution.

In FIG. 1, the first citrate compound may be added to a gold solution. In one implementation, the first citrate compound may be sodium citrate. In another implementation, the first citrate compound may be a salt with the citrate ion. In another implementation, the first citrate compound may be potassium citrate. In yet another implementation, the first citrate compound may be citric acid. In this implementation, the first citrate compound may be added to the gold solution, resulting in the reduction of gold, facilitated by the citrate ion of the first citrate compound. In one implementation, the first citrate compound may coat the gold in the gold solution and act as a capping agent. In another implementation, the first citrate compound may act to control the size of the gold core 102. In another implementation, the first citrate compound may act as a capping agent and contribute to the size of the gold core 102.

In FIG. 1, one implementation of an example process may include the use of a gold solution comprising a gold compound and a liquid. In one implementation, the liquid may be tap water, distilled water, or deionized water. For FIG. 1, yet another implementation of an example process may include using a liquid comprising ultrapure water. Ultrapure water may be water that has been treated in an ultrapurification process. The ultrapurification process provides highly pure water that can limit the salts in the water. Ultrapure water may also have reduced amounts of contaminants, including but not limited to organic and inorganic compounds, dissolved and particulate matter, volatiles and non-volatiles, reactive and inert substances, hydrophilic and hydrophobic substances, and dissolved gases. The pH and resistivity may be measured for the ultrapure water in order to check its quality.

In one implementation, the gold solution may comprise about 0.05% to about 5% gold chloride by weight. In another implementation, the gold solution may comprise about 95% to about 99.5% ultrapure water by weight. In one implementation, the gold solution may comprise gold chloride as the gold compound. Gold chloride, $HAuCl_4$ or $AuCl_{4-}$, may include Gold(I) chloride, Gold(III) chloride, Gold(I,III) chloride, or a combination of these chemicals. In another implementation, the gold solution may comprise chloroauric acid, $HAuCl_4$. During the process described, the formation of the gold core solution comprising the first citrate compound and the gold solution result in the formation at least one gold core.

In order to provide the silver shell around the gold core, a silver solution may be used. In one implementation, the silver solution may comprise ascorbic acid, a silver compound, and a strong base. In another implementation, the silver compound may comprise silver nitrate. In yet another implementation, the silver compound may comprise silver and a non-reactive portion of that silver compound. During the process described, a strong base may be used to adjust the pH to basic. In one implementation, the strong base may comprise sodium hydroxide. In another implementation, potassium hydroxide may be used as the strong base. During the process described, the silver solution comprising ascorbic acid, the silver compound, and the strong base react to form at least one silver shell.

After at least one silver shell has been added to the gold core, at least one particle may be separated from the gold core solution and dispersed in a liquid. In one implementation, the liquid may be may be tap water, distilled water, or deionized water. In another implementation, the liquid may be ultrapure water.

After at least one particle is dispersed in the liquid, a second citrate compound, hydroquinone, and a gold compound may be added to form an outer gold shell on top of the silver shell. In one implementation, the second citrate compound may comprise sodium citrate. In yet another implementation, the gold compound may comprise gold chloride.

The near-infrared wavelength absorption in the optical window exhibited by the example gold-silver-gold core-shell-shell nanoparticle of FIG. 1, ranging from about 800 nm to about 1300 nm, may provide a range where light can penetrate to a desired depth in biological tissues for photothermal therapy and non-invasive bio-imaging, resulting in a localized optical enhancement and photothermal effect when treating these biological tissues.

In one implementation, the gold-silver-gold core-shell-shell nanoparticles can be size-dependent and show significantly enhanced plasmonic properties. In another implementation for the nanoparticle, the ratio of the outer gold shell thickness to the overall particle size may provide a linear dependence with the position of the plasmon extinction peak wavelength. Temperature measurements after laser irradiation may show that the colloidal gold-silver-gold core-shell-shell nanoparticles have a higher photothermal effect compared to spherical gold nanoparticles and gold nanorods. In addition, the outer gold shell surface may allow for biological functionalization for cancer targeting and other technologies.

The gold-silver-gold core shell-shell nanoparticle provided by the process in FIG. 1 may be spherical or rod-shaped. In one implementation, the size of the core and shells can be tuned to obtain nanoparticles with diameters ranging from about 10 nm to about 200 nm. The optical properties of the nanoparticles are widely tunable and size-dependent. Additionally, the nanoparticles provided in FIG. 1 may be stable as a colloidal suspension in water. In FIG. 1, another implementation of the process may provide extended core-shell architectures with specially designed core and shell dimensions with multiple layers of shells. In still another implementation, the metallic gold-silver-gold core-shell-shell nanoparticle where the silver shell 104 and outer gold shell 106 can be relatively uniform thicknesses.

For the process shown in FIG. 1, one implementation may include the silver shell 104 configured to a desired width. In another implementation, additional silver shells and/or gold shells may be added during the process of forming the nanoparticles described in FIG. 1. In one implementation, the process may include at least the gold core 102, a silver shell 104, an outer gold shell 106 where additional silver shells and/or gold shells are added either: 1) between the silver shell 104 and outer gold shell 106; and/or 2) to the outer gold shell 106. In another implementation, at least two additional silver shells and/or gold shells may be added to the nanoparticle. Additional silver shells and/or gold shells may be added to provide different qualities to the nanoparticles. Additional silver shells and/or gold shells may also be added to increase the size or thickness of the nanoparticles. In one implementation, ascorbic acid, a silver compound, and a strong base may be used to form an additional silver shell. For example, an additional layer of silver may be formed on the silver shell 104 in order to increase the width of the silver shell 104 layer. In another example, the additional layer of silver may be formed by adding ascorbic acid, silver nitrate, and sodium hydroxide. In one implementation, another layer of silver may be introduced onto the silver shell 104 by adding ascorbic acid, silver nitrate, and sodium hydroxide. This additional layer of silver may be added while the particles are within the gold core solution or in another liquid. In one example, the liquid may be ultrapure water.

In FIG. 1, another implementation may include the outer gold shell 106 configured to a desired width. In one implementation, a second citrate compound, hydroquinone, and a gold compound may be used to form an additional gold shell. For example, an additional layer of gold may be formed on the outer gold shell 106 by the addition of the sodium citrate, hydroquinone, and gold chloride. The sodium citrate, hydroquinone, and gold chloride react to form the outer gold shell. The additional gold may be added to the outer gold shell 106 on the silver shell 104 or on top of any additional silver added to the silver shell 104. In one implementation, another layer of gold may be introduced onto the outer gold shell.

Figure 2:
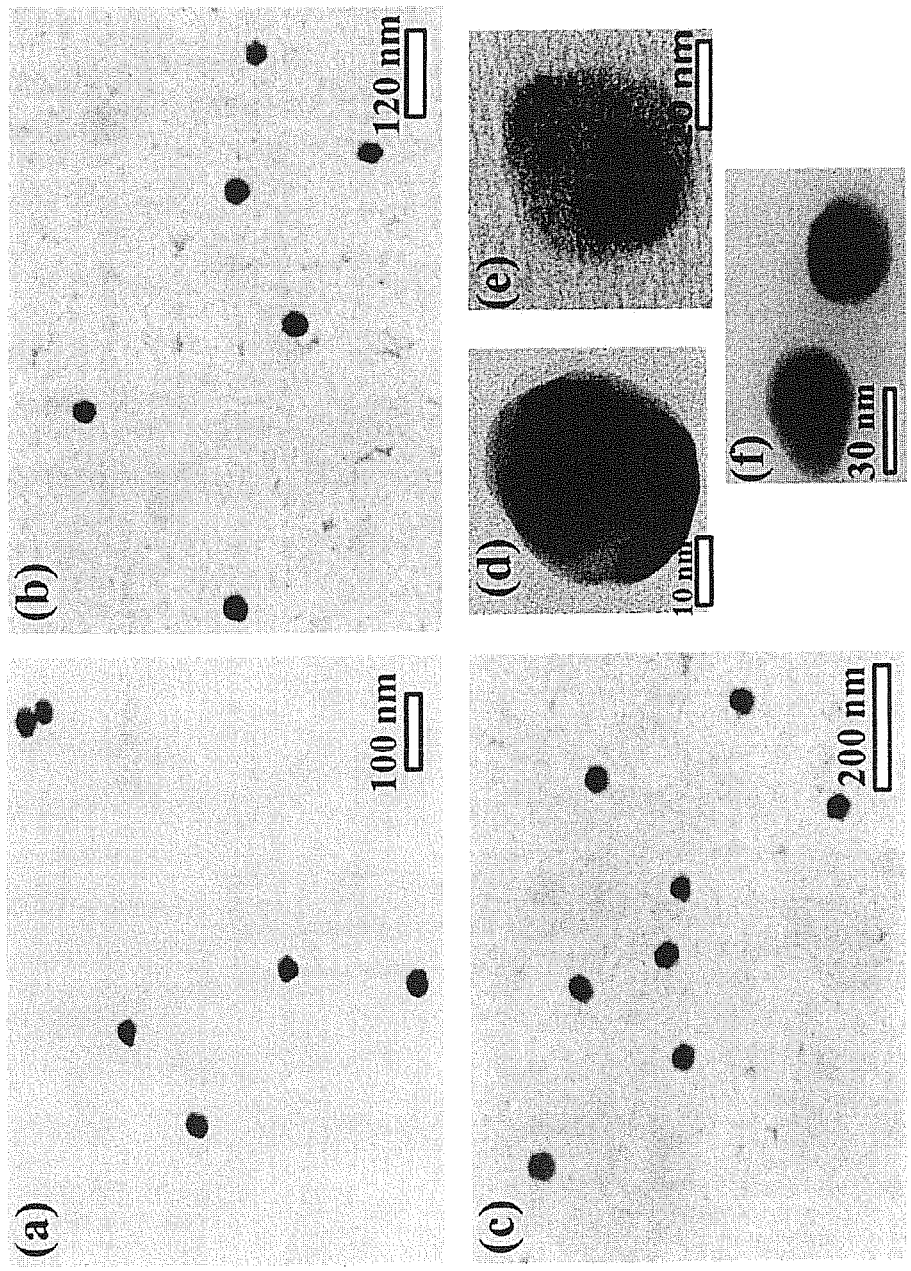
FIG. 2 illustrates characteristics of the nanoparticles prepared by the process described.

FIG. 2 provides several implementations of the core-shell-shell nanoparticles through high-resolution transmission electron microscopy (HR-TEM) with various core-shell-shell particle sizes. The HR-TEM, in addition to extinction spectroscopy and photothermal measurements, may be used to characterize the nanoparticles. The HR-TEM images of gold-silver-gold core-shell-shell nanoparticles provided in FIG. 2 provide an illustration of the nanoparticles with diameters of (a) 12-12-12 nm, (b) 12-18-10 nm, (c) 12-24-10 nm, (d) 12-12-5 nm, (e) 12-18-10 nm, and (f) 12-24-10 nm core-shell-shell sizes, respectively. The images provided in FIG. 2 (a)-(f) show selected HR-TEM images of the gold-silver-gold core-shell-shell nanoparticles with a 12±0.9 nm gold core and various silver and gold shell thicknesses. After the addition of the silver shell, the surface plasmon resonance peak may blueshift from 513 nm for the gold core to approximately 420 nm for the gold-silver core-shell nanoparticles. The plasmon extinction peak may then broaden, and may increase in intensity as the thickness of the silver shell is increased.

For the core-shell-shell nanoparticles such as those provided in FIG. 2, localized surface plasmon resonances, characterized by the coherent oscillations of free electrons under incident light, at the nanoparticles surface may be dependent on the nanoparticle composition, size, shape and surrounding medium. In one implementation, the plasmon resonances may lead to certain optical field enhancements. The plasmon extinction peak wavelength of the gold-silver-gold core-shell-shell nanoparticles may also depend on the ratio of the thickness of the outer gold shell to the overall size of the nanoparticle. In one implementation, the surface plasmon resonance peaks of these nanostructures can also be tuned from the visible to the near infrared wavelength region by controlling the dimensions of the core and the shells.

Figure 3:
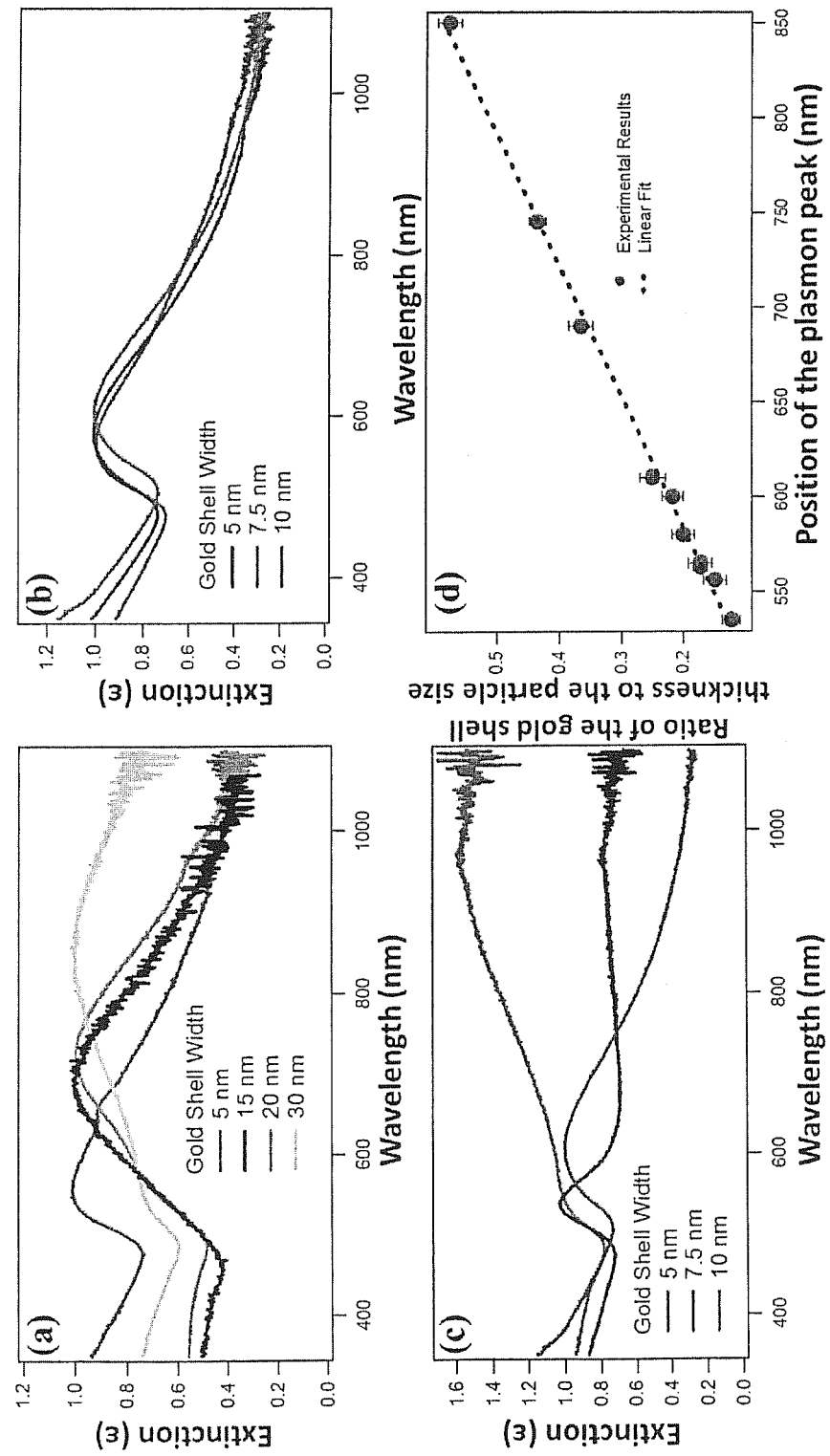
FIG. 3 illustrates characteristics of the nanoparticles prepared by the process described.

FIG. 3 may provide an example of the extinction spectra of the colloidal gold-silver-gold core-shell-shell nanoparticles with a 12±0.9 nm gold core and various silver and gold shell thicknesses. After the formation of the outer gold shell 106, the plasmon peak generally redshifts leading to enhanced extinction in the near-infrared wavelength region. FIG. 3(a) may illustrate the normalized extinction spectra of gold-silver-gold core-shell-shell nanoparticles with a 12±0.9 nm gold core 102, a 12±1.1 nm silver shell 104, and an outer gold shell 106 of thickness 5±0.6 nm, 15±0.9 nm, 20±1.6 nm, and 30±2.4 nm, respectively. For the thinnest gold shell of about 5 nm, the plasmon peak may be centered near about 565 nm and extends to the near-infrared wavelength region. As the thickness of the outer gold shell 106 may be increased, the plasmon peak may broaden and its maximum may progressively redshift to the near-infrared wavelength region. At an outer gold shell thickness of 30±2.4 nm, the plasmon peak may be centered near about 850 nm.

FIG. 3(b) may provide an additional example of the effect of varying the thickness of the silver shell 104. In one implementation, FIG. 3(b) may illustrate the extinction spectra of gold-silver-gold core-shell-shell nanoparticles with a 12±0.9 nm gold core, a 18±1.6 nm silver shell, and an outer gold shell thickness of 5±0.6 nm, 7.5±0.8 nm, and 10±1.1 nm, respectively. Similar to FIG. 3(a), the gold-shell-shell nanoparticles with the thinnest gold shell of about 5 nm may have a plasmon peak centered near about 565 nm that extends to the near-infrared wavelength region. In another implementation, increasing the thickness of the outer gold shell to a diameter of about 10 nm may redshift the plasmon peak wavelength to about 585 nm.

FIG. 3(c) may provide an example of the extinction spectra of the gold-silver-gold core-shell-shell nanoparticles with a 12±0.9 nm gold core, a 24±2.1 nm silver shell, and an outer gold shell thickness of 5±0.7 nm, 7.5±0.9 nm, and 10±1.1 nm, respectively. In one implementation for the thinnest gold shell of about 5 nm diameter, the plasmon peak may be centered at about 610 nm and may extend to the near-infrared wavelength region. In another implementation as the thickness of the gold shell may be increased, the plasmon peak may first blueshift, then an additional peak centered in the NIR may rise and increase in intensity. The plasmon-enhanced extinction spectra can be controlled from the UV to the NIR wavelengths by varying the silver and gold shell sizes, providing many biologically-relevant applications such as photothermal therapy and bioimaging.

As shown in FIG. 3(d), the plasmon extinction peak wavelength may vary with the ratio of thickness of the outer gold shell to the overall size of the nanoparticle. In the example for FIG. 3(d), the equation of the best fit line may be given by a slope of $1.44 \times 10^{-3}$ $2.9 \times 10^{-5}$ $nm^{-1}$ and a y-intercept of −0.64±0.02. In this example, varying the ratio of thickness of the outer gold shell to the overall size of the nanoparticle may provide a mechanism to control the plasmonic optical properties of the colloidal gold-silver-gold core-shell-shell nanoparticles with respect to the application.

Figure 4:
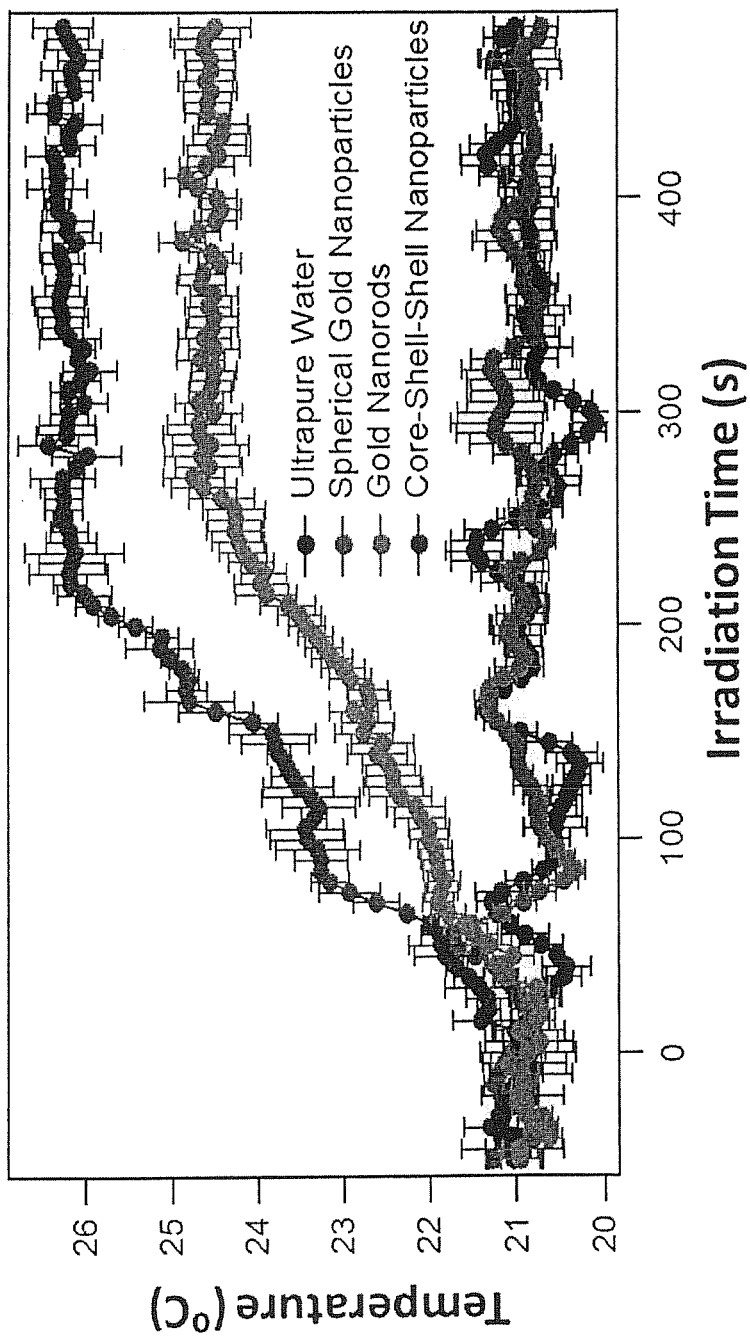
FIG. 4 illustrates characteristics of the nanoparticles prepared by the process described.

FIG. 4 provides a photothermal study of different nanoparticle samples. In this example, the temperature of the 54 nm colloidal gold-silver-gold core-shell-shell nanoparticle sample with a 12 nm core, a 12 nm silver shell, and a 20 nm outer gold shell as a function of time after irradiation with 800 nm laser light may be compared to corresponding measurements on colloidal gold nanorods with about a 10 nm width and about a 35 nm length in water, 54 nm spherical colloidal gold nanoparticles in water, and an ultrapure water control sample. The water and spherical colloidal gold nanoparticle samples may not exhibit any detectable temperature change after laser irradiation. In this example, the colloidal core-shell-shell nanoparticles show a temperature change of about 5.2±0.2° C. at a rate of about 1.5° C. per minute due to the conversion of the absorbed NIR light to heat by the plasmonic nanoparticles, and the gold nanorods show a temperature change of about 3.7±0.2° C. at a rate of about 0.75° C./min.

Figure 5:
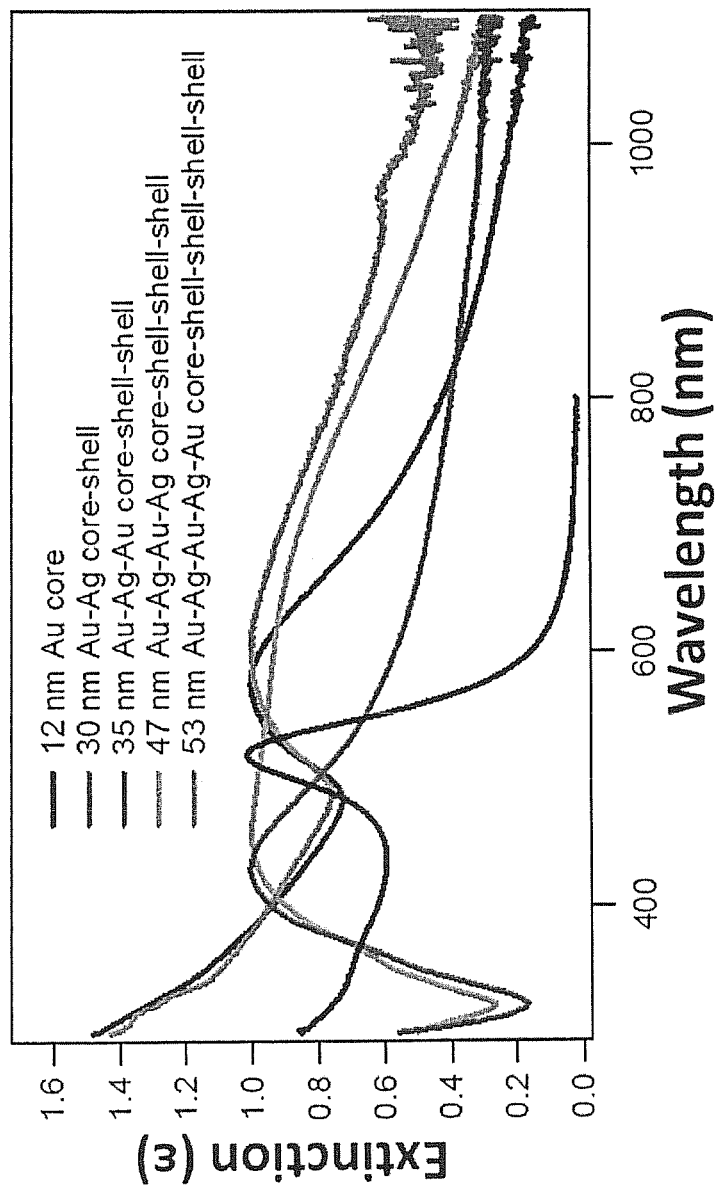
FIG. 5 illustrates characteristics of the nanoparticles prepared by the process described.

FIG. 5 provides an example of a normalized extinction spectra of 12 nm colloidal gold nanoparticles, 30 nm colloidal gold-silver core-shell nanoparticles, 35 nm colloidal gold-silver-gold core-shell-shell nanoparticles, 47 nm colloidal gold-silver-gold-silver core-shell-shell-shell nanoparticles, and 53 nm colloidal gold-silver-gold-silver-gold core-shell-shell-shell-shell nanoparticles, respectively. In this example, the plasmon extinction peak wavelength may correlate with the composition of the outer gold shell 106 of the nanoparticle. For example, when the outer shell composition is gold, the plasmon extinction peak wavelength ranges from about 550 to about 600 nm. However, if the outer shell is silver, the plasmon extinction peak wavelength ranges from about 400 to about 450 nm. In addition, every sequential shell of alternating gold or silver composition may broaden the plasmon extinction peak while redshifting it further to the NIR wavelengths. Further, the extinction peak wavelength of the extended gold-silver-gold-silver-gold nanoparticles with multiple alternating gold and silver shells may not follow trends shown in FIG. 3(d).

Figure 6:
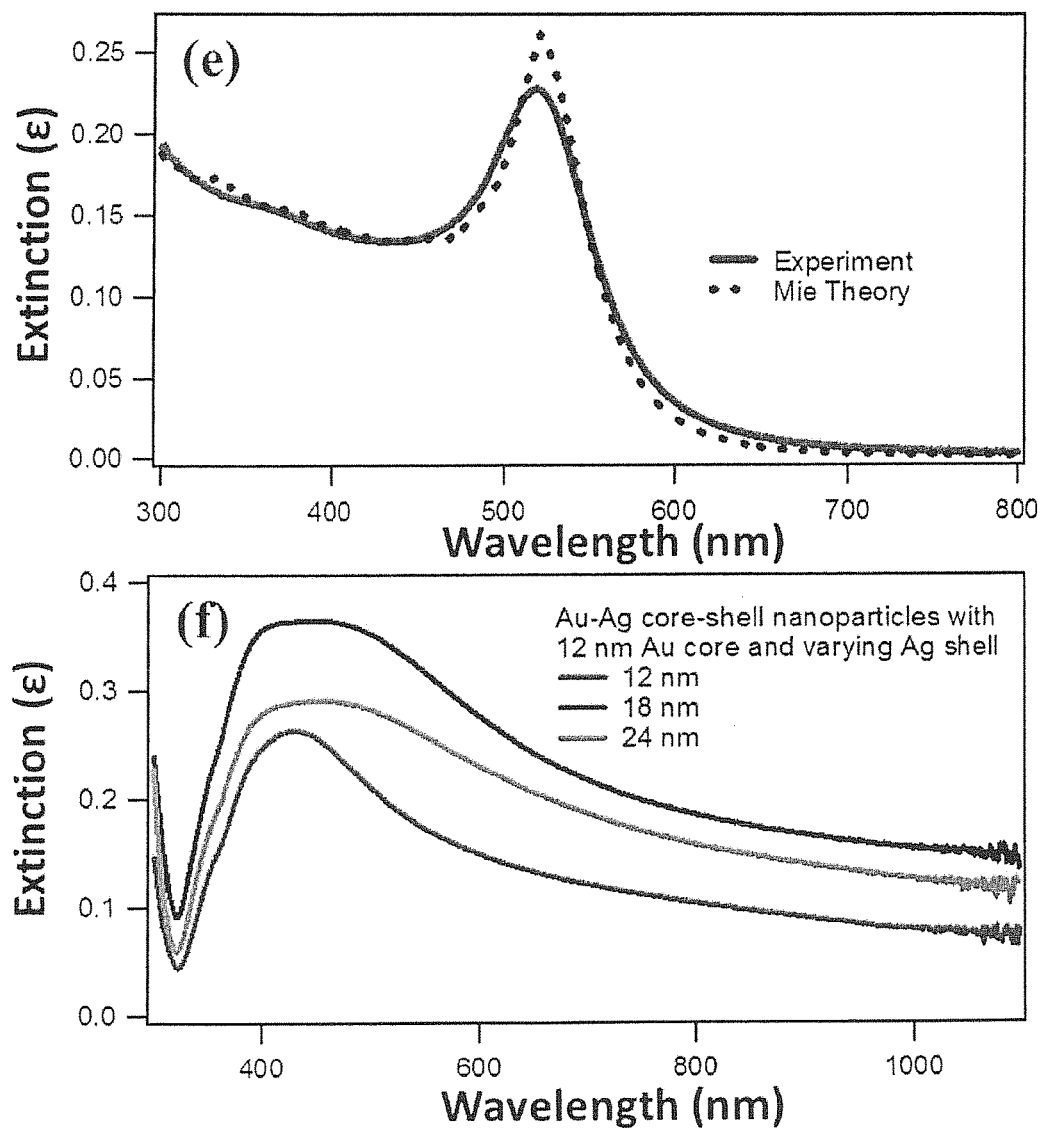
FIG. 6 illustrates characteristics of the nanoparticles prepared by the process described.

FIG. 6 provides additional examples of the extinction spectra of (e) 12 nm gold nanoparticles and (f) 24 nm, 30 nm, and 36 nm gold-silver core-shell nanoparticles. The extinction spectrum of the 12 nm colloidal gold nanoparticles may be fit for the light scattering of particles using Mie theory at a concentration is 2.9×1011 nanoparticles per milliliter.

Figure 7:
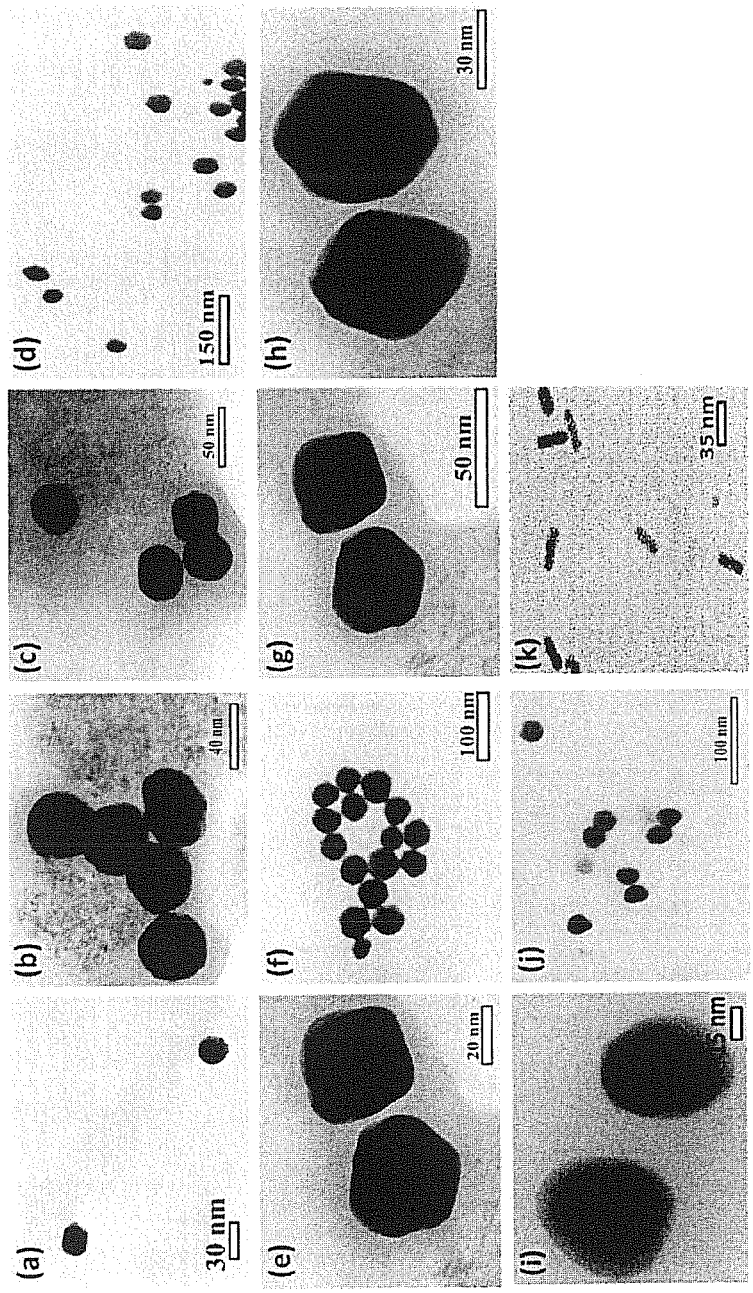
FIG. 7 illustrates characteristics of the nanoparticles prepared by the process described.

FIG. 7 provides additional examples of HR-TEM images of the gold-silver-gold core-shell-shell nanoparticle samples with different overall diameters of about (a) 29 nm, (b) 39 nm, (c) 44 nm, (d) 54 nm, (e) 35 nm, (f) 37.5 nm, (g) 40 nm, (h) 41 nm, (i) 44 nm, (j) 46 nm, respectively, and (k) gold nanorods of 10 nm width and 35 nm length.

Figure 8:
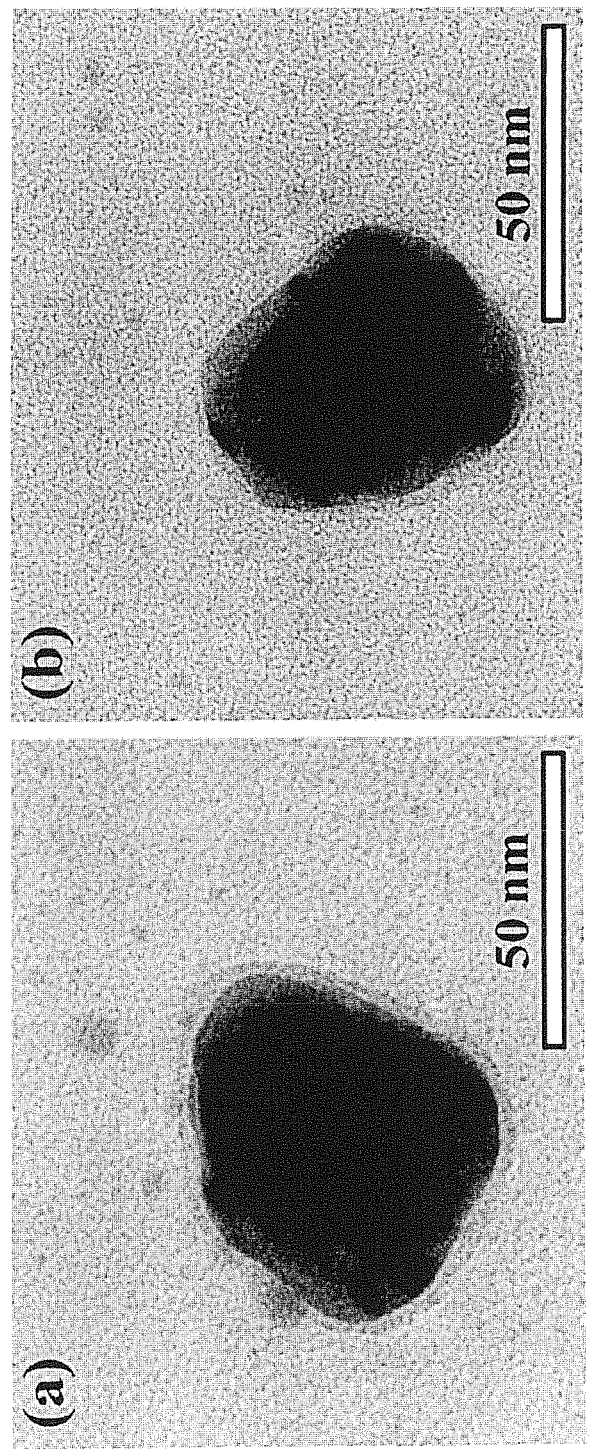
FIG. 8 illustrates characteristics of the nanoparticles prepared by the process described.

Similarly, FIG. 8 provides additional examples of HR-TEM images of the 53 nm gold-silver-gold-silver-gold core-shell-shell-shell-shell nanoparticles.

Figure 9:
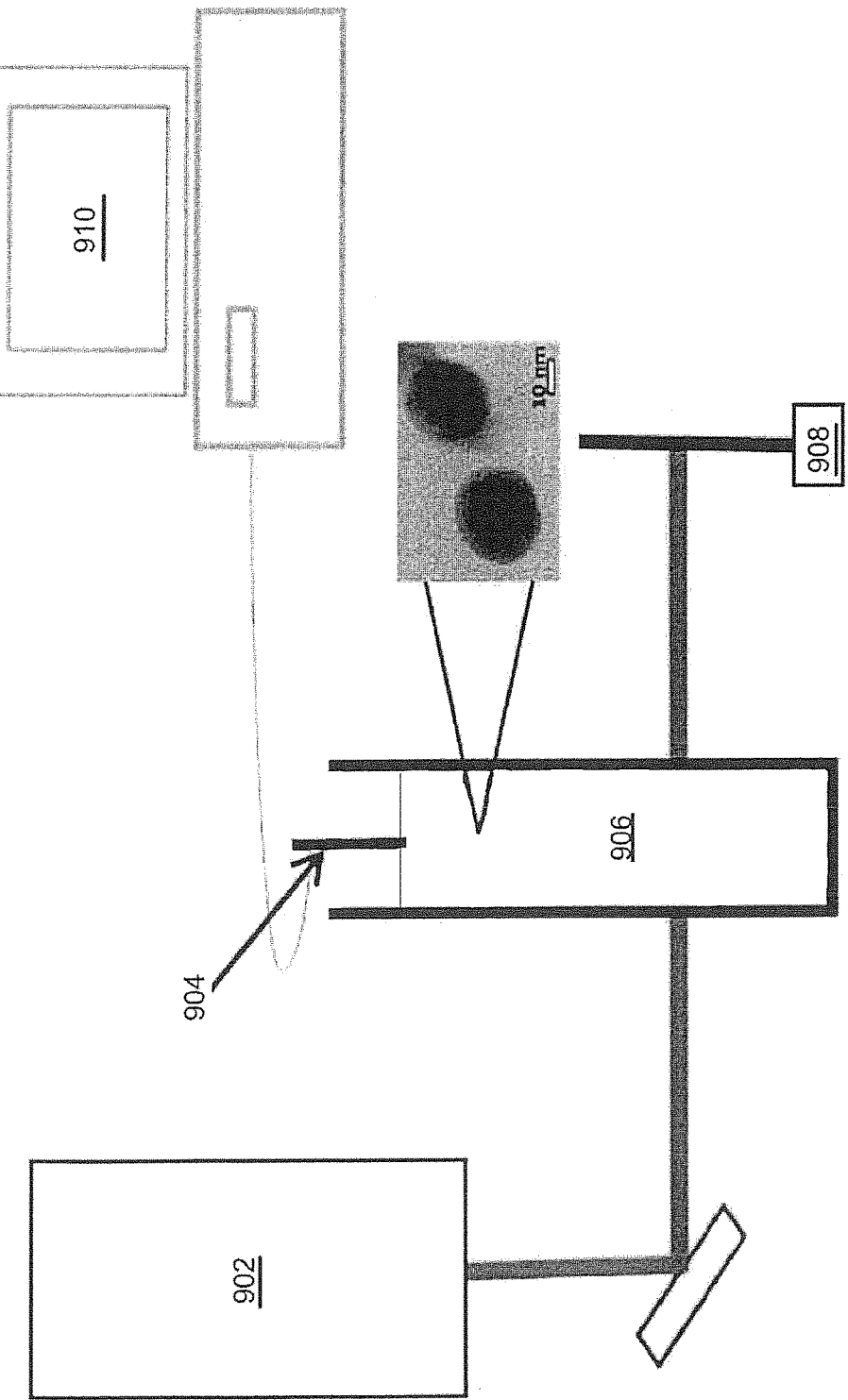
FIG. 9 illustrates characteristics of the nanoparticles prepared by the process described.

FIG. 9 shows a schematic diagram of the example experimental setup that may be used for a photothermal study. Within the diagram, an oscillator laser 902 may be transmitted through a solution comprising the core-shell-shell nanoparticles 906 where a thermocouple 904 and a computer 910 may be used for recording temperatures during the experimentation. In one implementation, the oscillator laser 902 made from titanium-sapphire may have an average power of about 2.6 W and 70 fs pulses centered at 800 nm with a repetition rate of 80 MHz and attenuated to 1.2 W. In another implementation, the oscillator laser 902 made from titanium-sapphire produces 0.7 mJ, 75 fs pulses centered at 800 nm with a repetition rate of 10 kHz. A beam block 908 can act as an optical filter and may absorb the 800 nm laser 902 provided for the experimentation.

Figure 10:
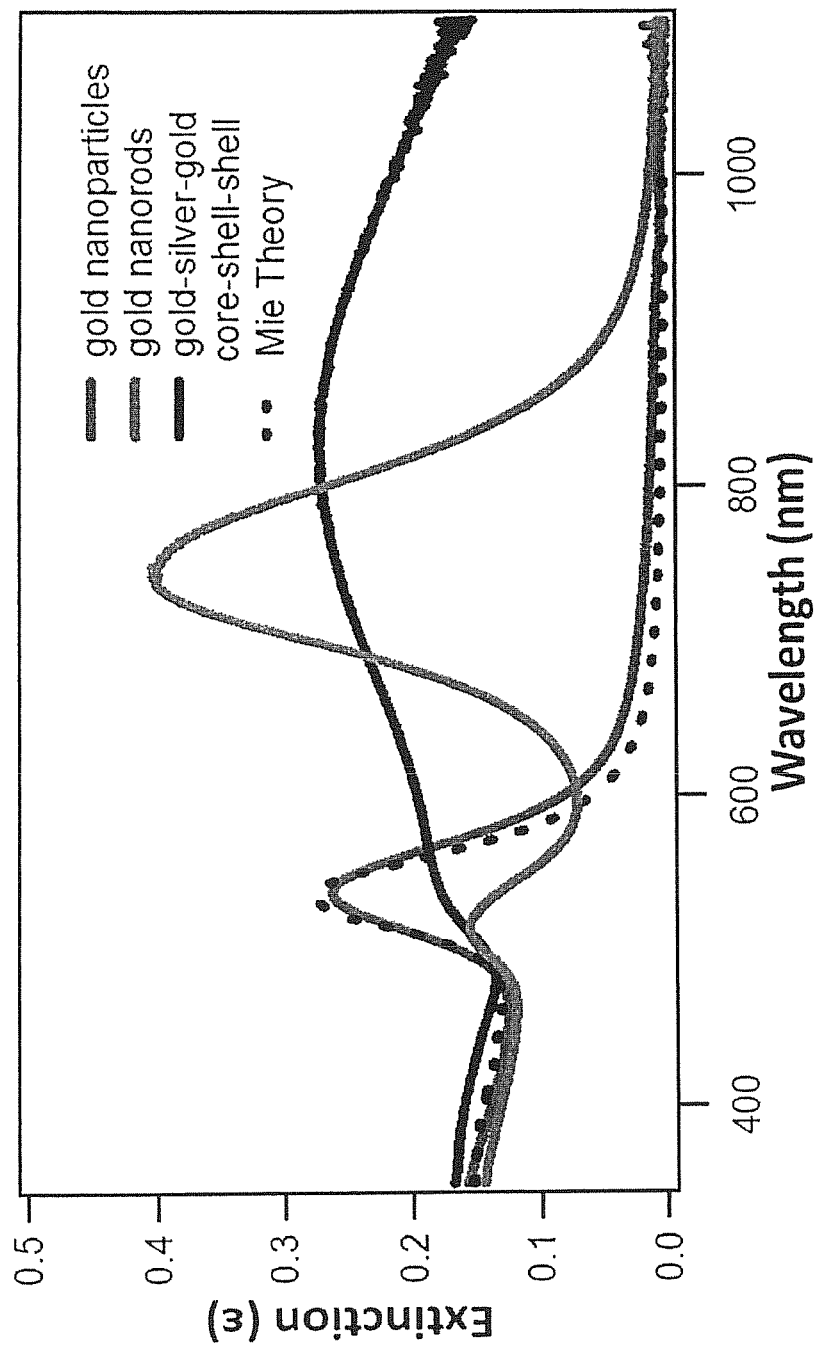
FIG. 10 illustrates characteristics of the nanoparticles prepared by the process described.

FIG. 10 provides yet another example of the extinction spectra of the 54 nm spherical colloidal gold nanoparticles, the colloidal gold nanorods (about 10 nm width and about 35 nm length) at a concentration of about $3.0 \times 10^{11}$ nanoparticles per milliliter, and the 54 nm colloidal gold-silver-gold core-shell-shell nanoparticles (sample CSS4) used in the photothermal study. The extinction of the spherical gold nanoparticles may be overlapped with the best fit using Mie theory (dotted black line) at a concentration of about $2.8 \times 10^{10}$ nanoparticles per milliliter.

Additionally, a functionalized group may be added to the gold-silver-gold core-shell-shell nanoparticles. The gold-silver-gold core-shell-shell nanoparticles can be thiolated and functionalized for potential biochemical applications and sensing applications. In one implementation, a functionalized group may be added when molecules with an exposed thiol may attach to the outer gold shell of the nanoparticle surface, forming a relatively strong gold-thiol bond. In another implementation, a range of molecular and biomolecular functionalization may be attached to the nanoparticle surface to improve biological stability and selectivity, depending on the desired application. In yet another implementation, functionalizations may include one or more of the following: mercaptosuccinic acid, polyethylene glycol, proteins, antibodies, antigens, micro RNA, pharmaceuticals, and fluorescent labels for improving biocompatibility, selective binding to biological targets, drug delivery, and/or molecular sensing applications.

Plasmonic gold and silver nanoparticles can be functionalized with biological molecules, polymers, and/or other groups through thiolation for applications in several applications, including biolabeling, drug delivery, and photothermal therapy. In one implementation, the outer gold shell may provide a surface for attaching biological molecules, such as proteins and DNA, for cell targeting and drug delivery.

Example 1

For the nanoparticle synthesis, all chemicals may be obtained from a single supplier, such as Sigma Aldrich, and used without further purification in ultrapure water. For the synthesis of 12 nm gold nanoparticle seeds for the gold core, 30 mL of 290 µM gold chloride in water is brought to reflux under vigorous stirring conditions, followed by the addition of 900 µL of 34 mM sodium citrate. The colloidal solution undergoes a color change from pale yellow to bright red after about 10 to about 20 minutes and is removed from heat and cooled to room temperature. For the growth of the first silver shell, 300 µL of the gold seeds are added to 10 mL ultrapure water. The mixture is kept at room temperature under vigorous stirring with additions of 60 µL of 100 mM ascorbic acid, 15 µL of 100 mM silver nitrate, and 75 µL of 100 mM sodium hydroxide. Ascorbic acid is a mild reducing agent that reduces Ag+ onto the gold core under basic conditions. The size of the silver shell can be controlled by selecting the number of ascorbic acid, silver nitrate, and sodium hydroxide sequential additions. The gold-silver core-shell colloidal nanoparticles are centrifuged at 2,400 rpm for 20 minutes and redispersed in 10 mL of ultrapure water. Different sizes of outer gold shells are then grown by adding 100 µL, 200 µL, or 300 µL of 29 mM gold chloride, followed by the addition of 25 µL of 34 mM sodium citrate and 100 µL of 0.03 M hydroquinone under vigorous stirring at room temperature for 60 minutes. These gold-silver-gold core-shell-shell nanoparticles can be easily thiolated and functionalized for potential biochemical applications. The three steps involved in the synthesis are represented in Scheme 1. Spherical gold nanoparticles and gold nanorods are used for comparison studies of the photothermal effects of the colloidal core-shell-shell nanoparticles. Spherical gold nanoparticles of diameter 54±6 nm are synthesized using a seeding growth technique reported previously. Here, 250 µL of the 12 nm seed solution, 100 µL of 0.03 M hydroquinone, and 22 µL of 34 mM sodium citrate are added consecutively to 10.0 mL of 2.9 mM gold chloride solution. The solution is left at room temperature and under vigorous stirring conditions for 60 minutes. The gold nanorod sample is obtained from a supplier, such as Nanopartz, has a 10 nm width, a 35 nm length, and is capped with cetyltrimethylammonium bromide in aqueous colloidal suspension.

Example 2

The photothermal performance of 54 nm colloidal gold-silver-gold core-shell-shell nanoparticles with a 12 nm gold core, a 12 nm silver shell, and a 30 nm outer gold shell are studied in solution under NIR light. A 0.8 mL volume of the colloidal sample is placed in a 1.0 mm path-length quartz cuvette and irradiated with a laser beam centered at 800 nm with an average power of 1.7 W, a beam size of 1.2±0.2 mm, a pulse width of 75 femtosecond (abbreviated as fs), and a repetition rate of 80 MHz. The temperature change is measured using a K type thermocouple connected to a computer using a data acquisition card. The results are compared to an ultrapure water sample, the 54±6 nm spherical colloidal gold nanoparticle sample at a concentration of $2.8 \times 10^{10}$ nanoparticles/mL in water, and the gold nanorods sample at a concentration of $3.0 \times 10^{11}$ nanoparticles/mL. The optical density (OD=0.26) of the plasmon peak of the 54 nm spherical colloidal gold nanoparticles at 540 nm is equal to the optical density of the plasmon peak of the gold-silver-gold core-shell-shell nanoparticle sample at 800 nm as well as the gold nanorod sample at 800 nm for a quantitative comparison of the photothermal effects of the different nanoparticle samples. The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A metallic nanoparticle made by the process of:
adding a first citrate compound to a gold solution resulting in a gold core solution from comprising at least one gold core;
adding ascorbic acid, a silver compound, and a strong base to the gold core solution resulting in a silver shell on at least one gold core; and
adding a second citrate compound, hydroquinone, and a gold compound to at least one silver shell on at least one gold core resulting in an outer gold shell on the silver shell.

2. The metallic nanoparticle of claim 1, wherein the nanoparticle is spherical.

3. The metallic nanoparticle of claim 1, wherein the diameter of the nanoparticle is about 10 nm to about 200 nm.

4. The metallic nanoparticle of claim 1, further comprising a functionalized group.

5. The metallic nanoparticle of claim 1, further comprising at least one additional gold shell to the outer gold shell of the metallic nanoparticle.

6. The nanoparticle of claim 1, further comprising at least one additional silver shell to the outer gold shell of the metallic nanoparticle.

7. A metallic nanoparticle comprising:
a gold core;
a silver shell; and
an outer gold shell.

* * * * *